US012564603B2

(12) United States Patent
Lee et al.

(10) Patent No.: US 12,564,603 B2
(45) Date of Patent: Mar. 3, 2026

(54) METHODS FOR INHIBITING PATHOGENIC INFECTION AND INHIBITING GROWTH OF PATHOGENS

(71) Applicant: Daily Digital Co., LTD., Kaohsiung City (TW)

(72) Inventors: Ming-Lang Lee, Kaohsiung City (TW); Chuan-Te Yen, Kaohsiung City (TW); Yan-Jun Wen, Kaohsiung City (TW); Hsiu-Hui Hung, Kaohsiung City (TW)

(73) Assignee: Daily Digital Co., Ltd., Kaohsiung City (TW)

( * ) Notice: Subject to any disclaimer, the term of this patent is extended or adjusted under 35 U.S.C. 154(b) by 0 days.

(21) Appl. No.: 17/736,443

(22) Filed: May 4, 2022

(65) Prior Publication Data

US 2022/0354883 A1    Nov. 10, 2022

(30) Foreign Application Priority Data

May 7, 2021    (TW) ............................ TW110116583
Mar. 29, 2022    (TW) ............................ TW111111937

(51) Int. Cl.
A61K 31/795 (2006.01)
A01N 43/90 (2006.01)
A01P 1/00 (2006.01)
A61P 31/00 (2006.01)

(52) U.S. Cl.
CPC ............ *A61K 31/795* (2013.01); *A01N 43/90* (2013.01); *A01P 1/00* (2021.08); *A61P 31/00* (2018.01)

(58) Field of Classification Search
CPC .................................................. A61K 31/795
See application file for complete search history.

(56) References Cited

U.S. PATENT DOCUMENTS 5,188,738 A  *  2/1993  Kaali ..................... A61L 2/0011
                                                  210/243
2023/0293576 A1 *  9/2023  Jones ..................... A01N 41/04
                                                  424/78.35

FOREIGN PATENT DOCUMENTS

WO    WO2020008000 A1 *  1/2020

OTHER PUBLICATIONS

Lopes et al. Overcoming Barriers to Preventing and Treating P. aeruginosa Infections Using AAV Vectored Immunoprophylaxis. (Year: 2022).*
Youngsang et al. (Antibacterial Poly (3,4-ethylenedioxythiophene): Poly(styrene-sulfonate)/Agarose Nanocomposite Hydrogels with Thermo-processability and Self-healing) (Year: 2018).*
Stöcker et al. (Why Does the Electrical Conductivity in Pedot: PSS Decrease with PSS Content? A Study Combining Thermoelectric Measurements with Impedance Spectroscopy). (Year: 2012).*
Khatoon et al. (Bacterial biofilm formation on implantable devices and approaches to its treatment and prevention) (Year: 2018).*
Namsheer et al. (Conducting polymers: a comprehensive review on recent advances in synthesis, properties and applications). (Year: 2020).*
Badylak et al. (Photodynamic Inactivation of Pseudorabies Virus with Methylene Blue Dye, Light and Electricity). (Year: 1982).*
Kim et al. (Enhancement of electrical conductivity of poly(3,4-ethylenedioxythiophene)/poly(4-styrenesulfonate) by a change of solvents). (Year: 2001).*
Subathra et al. Suggesting a new combination of antiviral agents: Targeting the Herpes Simplex Virus. Journal of Applied Pharmacuei-cal Science vol. 4(09) pp. 114-119. September (Year: 2014).*
Kontarov et al. (The study of the antiviral activity of polyelectrolytes with respect to the influenza virus), (Year: 2019).*
Mahat et al. (Potential Applications of Conducting Polymers to Reduce Secondary Bacterial Infections among COVID-19 Patients: A Review). Feb. (Year: 2021).*

* cited by examiner

*Primary Examiner* — Sarah Alawadi
(74) *Attorney, Agent, or Firm* — Nixon & Vanderhye, P.C.

(57) ABSTRACT

Disclosed herein are methods for inhibiting pathogenic infection and inhibiting growth of pathogens using a conductive polymer material including a conductive component. The conductive component contains poly(3,4-ethylenedioxythiophene)-poly(styrenesulfonate), and a molar ratio of poly(3,4-ethylenedioxythiophene) to poly(styrenesulfonate) in the poly(3,4-ethylenedioxythiophene)-poly(styrenesulfonate) ranges from 1:1 to 1:25.

14 Claims, No Drawings

METHODS FOR INHIBITING PATHOGENIC INFECTION AND INHIBITING GROWTH OF PATHOGENS

CROSS-REFERENCE TO RELATED APPLICATION

This application claims priority of Taiwanese Invention Patent Application No. 110116583, filed on May 7, 2021, and Taiwanese Invention Patent Application No. 111111937, filed on Mar. 29, 2022.

FIELD

The present disclosure relates to methods for inhibiting pathogenic infection and inhibiting growth of pathogens using a conductive polymer material including a conductive component.

BACKGROUND

Various pathogens existing in the environment can affect human health and cause various diseases. Therefore, the demand for substances with antibacterial and antiviral functions has been increasing. Common substances with antibacterial and antiviral functions include nanogold solutions, nanosilver solutions, and molecular enzymes (also known as VirusBom). However, nanogold and nanosilver cannot be excreted by the human body, causing the problem of being accumulated in the body. In addition, the molecular enzymes (i.e., VirusBom) must react with bacteria or viruses for a long time in order to achieve antibacterial or antiviral effect.

SUMMARY

Therefore, in a first aspect, the present disclosure provides a method for inhibiting pathogenic infection which can alleviate at least one of the drawbacks of the prior art.

The method includes administering to a subject in need thereof a conductive polymer material including a conductive component. The conductive component contains poly(3,4-ethylenedioxythiophene)-poly(styrenesulfonate), and a molar ratio of poly(3,4-ethylenedioxythiophene) to poly(styrenesulfonate) in the poly(3,4-ethylenedioxythiophene)-poly(styrenesulfonate) ranges from 1:1 to 1:25.

In a second aspect, the present disclosure provides a method for inhibiting growth of pathogens, which can alleviate at least one of the drawbacks of the prior art, and which includes applying the aforesaid conductive polymer material onto an object.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure.

Indeed, the present disclosure is in no way limited to the methods and materials described.

The present disclosure provides a method for inhibiting pathogenic infection, which includes administering to a subject in need thereof a conductive polymer material including a conductive component.

The conductive component contains poly(3,4-ethylenedioxythiophene)-poly(styrenesulfonate), and a molar ratio of poly(3,4-ethylenedioxythiophene) to poly(styrenesulfonate) in the poly(3,4-ethylenedioxythiophene)-poly(styrenesulfonate) ranges from 1:1 to 1:25.

Antibacterial and antiviral tests have proved that the conductive polymer material can inhibit or even kill pathogenic bacteria and pathogenic viruses, and hence can be used for antibacterial and antiviral applications.

As used herein, the term "administration" or "administering" means introducing, providing or delivering a predetermined active ingredient to a subject by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human.

In certain embodiments, the conductive polymer material further includes dimethyl sulfoxide, and a weight ratio of dimethyl sulfoxide to the conductive component is 1:33.

In certain embodiments, the conductive component further contains water.

In certain embodiments, the molar ratio of poly(3,4-ethylenedioxythiophene) to poly(styrenesulfonate) in the poly(3,4-ethylenedioxythiophene)-poly(styrenesulfonate) ranges from 1:1.5 to 1:5.

According to the present disclosure, the pathogenic infection is caused by a pathogenic bacterium selected from the group consisting of antibiotic-resistant *Staphylococcus aureus, Pseudomonas aeruginosa, Escherichia coli, Candida albicans*, and combinations thereof.

According to the present disclosure, the pathogenic infection is caused by a pathogenic virus selected from the group consisting of enterovirus, paramyxovirus, coronavirus, herpes simplex virus, influenza virus, and combinations thereof.

In certain embodiments, the enterovirus is enterovirus 71 (EV71). In certain embodiments, the paramyxovirus is newcastle disease virus (NDV). In certain embodiments, the coronavirus is selected from the group consisting of feline infectious peritonitis virus (FIPV) and transmissible gastroenteritis virus (TGEV). In certain embodiments, the herpes simplex virus is pseudorabies virus (PRV). In certain embodiments, the influenza virus is selected from the group consisting of influenza A virus and influenza B virus.

According to the present disclosure, the conductive polymer material may be prepared in the form of a pharmaceutical composition. The pharmaceutical composition may be formulated into a dosage form suitable for topical administration using technology well known to those skilled in the art.

According to the present disclosure, the dosage form suitable for topical administration includes, but is not limited to, emulsions, gels, ointments, creams, patches, liniments, powders, aerosols, sprays, lotions, serums, pastes, foams, drops, suspensions, salves, and bandages.

The present disclosure also provides a method for inhibiting growth of pathogens, which includes applying the aforesaid conductive polymer material onto an object.

Examples of the object may include, but are not limited to, a metal object and a plastic object.

According to the present disclosure, the pathogens are selected from the group consisting of antibiotic-resistant *Staphylococcus aureus, Pseudomonas aeruginosa, Escherichia coli, Candida albicans*, and combinations thereof.

According to the present disclosure, the pathogens are selected from the group consisting of enterovirus, paramyxovirus, coronavirus, herpes simplex virus, influenza virus, and combinations thereof.

In certain embodiments, the enterovirus is enterovirus 71 (EV71). In certain embodiments, the paramyxovirus is newcastle disease virus (NDV). In certain embodiments, the coronavirus is selected from the group consisting of feline infectious peritonitis virus (FIPV) and transmissible gastroenteritis virus (TGEV). In certain embodiments, the herpes simplex virus is pseudorabies virus (PRV). In certain embodiments, the influenza virus is selected from the group consisting of influenza A virus and influenza B virus.

The disclosure will be further described by way of the following examples. However, it should be understood that the following examples are solely intended for the purpose of illustration and should not be construed as limiting the disclosure in practice.

EXAMPLES

Preparation of Conductive Polymer Materials

Example 1 (EX1)

153.25 g of poly(styrenesulfonate)(abbreviated as PSS) (Manufacturer: AkzoNobel; Molecular weight: 70000) was mixed with 3923.026 g of water, followed by stirring at 40° C. for 30 minutes. The resultant mixture was mixed with 0.811 g of ferric chloride (FeCl₃) (Alfa Aesar), and was then stirred at 40° C. for 30 minutes, followed by adding 7.109 g of 3,4-ethylenedioxythiophene (EDOT) (Junhan Biochemical Co., Ltd.). The resultant mixture was allowed to undergo a reaction at 40° C. for 20 minutes under stirring. After the temperature of the reactant dropped to 20° C., 6.3895 g of ammonium persulfate (($NH_4)_2S_2O_8$) (ADEKA) was added, and was then stirred for 120 minutes. The above steps of adding ammonium persulfate and then stirring were repeated twice.

Next, the resultant mixture was added with 39.09 g of strong-acid cation exchange resin (Manufacturer: Tai-Young Chemical Co., Ltd.; Catalogue no.: DIAION UBK08H; Ingredient: styrene polymer) and 55.54 g of weak-base anion exchange resin (Manufacturer: Tai-Young Chemical Co., Ltd.; Catalogue no.: RELITE JA310; Ingredient: styrene-divinylbenzene copolymer), and was then stirred for 60 minutes. The resultant mixture was subjected to filtration using a filter (mesh: 200 μm), so as to obtain a conductive component. The conductive component contained poly(3,4-ethylenedioxythiophene)-poly(styrenesulfonate) and water.

The molar ratio of poly(3,4-ethylenedioxythiophene) to poly (styrenesulfonate) in the poly(3,4-ethylenedioxythiophene)-poly(styrenesulfonate) was 1:5.

The conductive component was subjected to a homogenization treatment 10 times using a high-pressure homogenizer (Manufacturer: GOGENE Co., Ltd.; Catalogue no.: N-10) under a pressure of 1800 bar, so as to obtain a conductive polymer material with uniform particle size.

Examples 2 to 3 (EX2 to EX3)

The procedures for preparing the conductive polymer materials of EX2 to EX3 were similar to those of EX1, except that the amounts of water, EDOT, ($NH_4)_2S_2O_8$, strong-acid cation exchange resin, and weak-base anion exchange resin were varied as shown in Table 1 below.

Example 4 (EX4)

The procedures for preparing the conductive polymer materials of EX4 were similar to those of EX2, except that after conducting the homogenization treatment 10 times, 0.903 g of dimethyl sulfoxide was added.

Example 5 (EX5)

The procedures for preparing the conductive polymer materials of EX5 were similar to those of EX3, except that after conducting the homogenization treatment 10 times, 0.671 g of dimethyl sulfoxide was added.

The components and the amounts thereof for making the conductive polymer materials of EX1 to EX5 are summarized in Table 1 below.

Measurement of Solid Content

A respective one of the conductive polymer materials of EX1 to EX5 was subjected to a drying treatment in an oven (Manufacturer: DENGYNG; Catalogue no.: DO30) at 105° C. for 3 hours, so as to obtain a dried powder of the conductive polymer material.

The weights of the dried powder of the conductive polymer materials and conductive polymer materials of EX1 to EX5 were measured. The solid content (%) was calculated using the following Equation (I):

$$A=(B/C)\times100 \tag{I}$$

where A=solid content (%)

B=weight of the dried powder of the conductive polymer material of respective Example (g)

C=weight of the conductive polymer material of respective Example (g)

The results are shown in Table 1 below. It can be seen from Table 1 that a respective one of the conductive polymer materials of EX1 to EX5 had a solid content of 1.3 wt %.

TABLE 1

| Component (g) | EX1 | EX2 | EX3 | EX4 | EX5 |
|---|---|---|---|---|---|
| Poly (styrenesulfonate) | 153.250 | 76.625 | 50.879 | 76.625 | 50.879 |
| Water | 3923.026 | 2231.381 | 1662.989 | 2231.381 | 1662.989 |
| FeCl₃ | 0.811 | 0.811 | 0.811 | 0.811 | 0.811 |
| EDOT | 7.109 | 7.109 | 7.109 | 7.109 | 7.109 |
| ($NH_4)_2S_2O_8$ | 12.779 | 12.779 | 12.779 | 12.779 | 12.779 |
| Strong-acid cation exchange resin | 39.09 | 58.00 | 78.54 | 58.00 | 78.54 |
| Weak-base anion exchange resin | 55.54 | 91.70 | 130.13 | 91.70 | 130.13 |

TABLE 1-continued

| Component (g) | EX1 | EX2 | EX3 | EX4 | EX5 |
|---|---|---|---|---|---|
| Total weight of conductive component | 53.084 | 30.097 | 22.373 | 30.097 | 22.373 |
| Dimethyl sulfoxide | 0 | 0 | 0 | 0.903 | 0.671 |
| Molar ratio of poly (3,4-ethylenedioxythiophene) to poly (styrenesulfonate) | 1:5 | 1:2.5 | 1:1.66 | 1:2.5 | 1:1.66 |
| Solid content (%) | 1.3 | 1.3 | 1.3 | 1.3 | 1.3 |

Analysis of Antibacterial Activity

The antibacterial activity of the conductive polymer material of EX3 was analyzed according to U.S. Pharmacopeia 26 NF 21 Microbiological Tests (51) Antimicrobial Effectiveness Testing which was entrusted to SGS Co., Ltd., Taiwan.

Four pathogenic bacterial strains used in this experiments are readily available to the public, and were purchased from the American Type Culture Collection (ATCC, Manassas, Va., USA). The relevant information regarding each of the pathogenic bacterial strains is listed in Table 2 below.

TABLE 2

| Pathogenic bacterial strains | Accession number |
|---|---|
| Antibiotic-resistant *Staphylococcus aureus* (MRSA) | ATCC 33591 |
| *Pseudomonas aeruginosa* | ATCC 9027 |
| *Escherichia coli* | ATCC 8739 |
| *Candida albicans* | ATCC 10231 |

The results show that, after cultivating with each of the four pathogenic bacterial strains for 24 hours, the conductive polymer material of EX3 has an inhibition rate of more than 99.9% against a respective one of antibiotic-resistant *Staphylococcus aureus*, *Pseudomonas aeruginosa*, and *Escherichia coli*, and has an inhibition rate of more than 65.4% against *Candida albicans*. Therefore, the applicant contemplates that the conductive polymer material of EX3 has an excellent antibacterial activity.

Analysis of Antiviral Activity

A. Source and Cultivation of Cell Lines

Five cell lines used in this experiments are readily available to the public, and were purchased from the Bioresource Collection and Research Center (BCRC) of the Food Industry Research and Development Institute (FIRDI) (No. 331, Shih-Pin Rd., Hsinchu City 300, Taiwan). The relevant information regarding each of the cell lines is listed in Table 3 below.

TABLE 3

| Cell lines | Accession number |
|---|---|
| Madin-Darby canine kidney (MDCK) cell line | BCRC 60004 |
| Rhabdomyosarcoma (RD) cell line | BCRC 60113 |
| Baby Hamster Syrian Kidney cell line BHK21 | BCRC 60041 |
| Crandell-Rees Feline Kidney Cell line CRFK | BCRC 60151 |
| Porcine kidney cell line PK-15 | BCRC 60057 |

A respective one of the five cell lines were grown in a 10-cm Petri dish containing Dulbecco's Modified Eagle's Medium (DMEM) supplemented with 10% fetal bovine serum (FBS) and 1% Gibco™ Penicillin-Streptomycin-Neomycin (PSN) Antibiotic Mixture. Next, the cells were cultivated in an incubator with culture conditions set at 37° C. and 5% $CO_2$ for 24 hours. The resultant cell cultures were used for the following experiments.

B. Source and Cultivation of Viruses

Six types of viruses used in this experiments were obtained from Graduate Institute of Animal Vaccine Technology, National Pingtung University of Science and Technology, Taiwan, and were cultivated using the corresponding cell line shown in Table 4 according to procedures known to those skilled in the art.

TABLE 4

| Virus | Cell line |
|---|---|
| Newcastle disease virus (isolate V158) | BHK21 cells |
| Enterovirus 71 (isolate EV71) | RD cells |
| Transmissible gastroenteritis virus (isolate TGE-1) | PK-15 cells |
| Feline infectious peritonitis virus (isolate FIP-1) | CRFK cells |
| Pseudorabies virus (Bartha) | PK-15 cells |
| Influenza A virus (isolate PR8) | MDCK cells |

Briefly, 1 mL of a respective one of the cell cultures of the five cell lines shown in Table 4 was seeded at a concentration of $2 \times 10^6$ cells/mL into a flask containing 9 mL of DMEM supplemented with 10% FBS, followed by cultivation in an incubator (37° C., 5% $CO_2$). When the cells formed a cell monolayer in the flask, the liquid medium was removed, and the respective resultant cell culture was washed with phosphate-buffered saline (PBS), and was then infected with a corresponding one of the six viruses as shown in Table 4 at a multiplicity of infection (m.o.i.) of 0.1, followed by being left standing for 1 hour. Next, 5 mL of DMEM was added into the flask, followed by cultivation in an incubator (37° C., 5% $CO_2$). The cultured cells were observed daily for cytopathic effect. Freeze-thaw treatment was performed 3 times when cytopathic effect was observed in 75% of the cultured cells, so as to obtain a liquid culture. After centrifugation at 2,500 g and 4° C. for 10-20 minutes, the resultant supernatant was collected and stored at −80° C. until use. The supernatant is referred to as "virus fluid" hereinafter.

C. Preparation of Test Sample

A respective one of the conductive polymer materials of EX1 to EX5 was subjected to dilution with PBS, so as to obtain 7 dilutions (prepared using dilution factors of 1, 2, 4, 8, 16, 32, and 64). Then, a respective one of the dilutions was incubated with each of the virus fluids prepared in section B for different incubation times (i.e., 0.5, 1, 2, 5, 10, 20, 30, and 60 minutes). The respective resultant mixture was used as a test sample, and was subjected to the following analyses.

D. Plaque Reduction Assay (PRA)

A respective one of the cell cultures of the five cell lines shown in Table 4 above was incubated in a respective well of a 6-well culture plate containing mL of DMEM supplemented with 10% FBS at $3×10^5$ cells/well, followed by cultivation in an incubator (37° C., 5% $CO_2$) for 1 day. Afterwards, each of the cell cultures was treated with 100 μL of the test sample prepared using the corresponding virus fluid as shown in Table 4, followed by cultivation in an incubator (37° C.) for 1 hour. 2 mL of a semi-solid overlay medium (42° C.) was added to each well, followed by cultivation in an incubator (37° C., 5% $CO_2$) for 5 days. Next, 2 mL of a crystal violet-containing staining solution was added to each well, followed by being left standing for 0.5 hour. Then, each well was washed with water to remove the staining solution, followed by air-drying to obtain a specimen.

The color change of the respective specimen was visually observed. The specimen, if colorless, indicates that the virus was alive. The specimen, if exhibiting crystal violet color, indicates that the virus had been completely killed.

The results are shown in Tables 5 to 9 below. It can be seen from Table 5 that the conductive polymer material of EX1 exhibited antiviral activity against newcastle disease virus, feline infectious peritonitis virus, transmissible gastroenteritis virus, pseudorabies virus, and influenza A virus. In particular, under the same dilution factor, the conductive polymer material of EX1 exhibited antiviral activity against newcastle disease virus and influenza A virus in a relatively short period of time.

It can be seen from Table 6 that the conductive polymer material of EX2 exhibited antiviral activity against feline infectious peritonitis virus, transmissible gastroenteritis virus, and pseudorabies virus.

It can be seen from Table 7 that the conductive polymer material of EX3 exhibited antiviral activity against enterovirus 71, newcastle disease virus, feline infectious peritonitis virus, transmissible gastroenteritis virus, pseudorabies virus, and influenza A virus. In particular, under the same dilution factor, the conductive polymer material of EX3 exhibited antiviral activity against newcastle disease virus, pseudorabies virus, and influenza A virus in a relatively short period of time.

It can be seen from Table 8 that the conductive polymer material of EX4 exhibited antiviral activity against feline infectious peritonitis virus, transmissible gastroenteritis virus, and pseudorabies virus. In particular, under the same dilution factor, the conductive polymer material of EX4 exhibited antiviral activity against pseudorabies virus in a relatively short period of time.

It can be seen from Table 9 that the conductive polymer material of EX5 exhibited antiviral activity against newcastle disease virus, feline infectious peritonitis virus, transmissible gastroenteritis virus, pseudorabies virus, and influenza A virus. In particular, under the same dilution factor, the conductive polymer material of EX5 exhibited antiviral activity against pseudorabies virus in a relatively short period of time.

TABLE 5

| Conductive polymer material of EX1 | | | |
|---|---|---|---|
| Virus | Dilution factor | Incubation time (minute) | Antiviral activity |
| Newcastle disease virus | 2 | 5 | Completely killed |
| | 4 | 5 | Completely killed |
| | 8 | 5 | Completely killed |
| | 8 | 10 | Completely killed |
| | 8 | 20 | Completely killed |
| | 8 | 30 | Completely killed |
| | 8 | 60 | Completely killed |
| Transmissible gastroenteritis virus | 2 | 60 | Completely killed |
| | 4 | 60 | Completely killed |
| | 8 | 60 | Completely killed |
| | 16 | 60 | Completely killed |
| | 32 | 60 | Completely killed |
| | 64 | 60 | Completely killed |
| Feline infectious peritonitis virus | 2 | 60 | Completely killed |
| | 4 | 60 | Completely killed |
| | 8 | 60 | Completely killed |
| | 16 | 60 | Completely killed |
| | 32 | 60 | Completely killed |
| | 64 | 60 | Completely killed |
| Pseudorabies virus | 2 | 60 | Completely killed |
| | 4 | 60 | Completely killed |
| | 8 | 60 | Completely killed |
| | 16 | 60 | Completely killed |
| | 32 | 60 | Completely killed |
| | 64 | 60 | Completely killed |
| Influenza A virus | 2 | 5 | Completely killed |
| | 4 | 5 | Completely killed |
| | 8 | 5 | Completely killed |
| | 8 | 10 | Completely killed |
| | 8 | 20 | Completely killed |
| | 8 | 30 | Completely killed |
| | 8 | 60 | Completely killed |

TABLE 6

Conductive polymer material of EX2

| Virus | Dilution factor | Incubation time (minute) | Antiviral activity |
|---|---|---|---|
| Transmissible gastroenteritis virus | 2 | 60 | Completely killed |
| | 4 | 60 | Completely killed |
| | 8 | 60 | Completely killed |
| | 16 | 60 | Completely killed |
| Feline infectious peritonitis virus | 2 | 60 | Completely killed |
| | 4 | 60 | Completely killed |
| | 8 | 60 | Completely killed |
| | 16 | 60 | Completely killed |
| Pseudorabies virus | 2 | 60 | Completely killed |
| | 4 | 60 | Completely killed |
| | 8 | 60 | Completely killed |
| | 16 | 60 | Completely killed |
| | 32 | 60 | Completely killed |
| | 64 | 60 | Completely killed |

TABLE 7

Conductive polymer material of EX3

| Virus | Dilution factor | Incubation time (minute) | Antiviral activity |
|---|---|---|---|
| Enterovirus 71 | 2 | 60 | Completely killed |
| Newcastle disease virus | 2 | 5 | Completely killed |
| | 4 | 5 | Completely killed |
| | 8 | 5 | Completely killed |
| | 8 | 10 | Completely killed |
| | 8 | 20 | Completely killed |
| | 8 | 30 | Completely killed |
| | 8 | 60 | Completely killed |
| Transmissible gastroenteritis virus | 2 | 60 | Completely killed |
| | 4 | 60 | Completely killed |
| | 8 | 60 | Completely killed |
| | 16 | 60 | Completely killed |
| Feline infectious peritonitis virus | 2 | 60 | Completely killed |
| | 4 | 60 | Completely killed |
| | 8 | 60 | Completely killed |
| | 16 | 60 | Completely killed |
| Pseudorabies virus | 2 | 5 | Completely killed |

TABLE 7-continued

Conductive polymer material of EX3

| Virus | Dilution factor | Incubation time (minute) | Antiviral activity |
|---|---|---|---|
| | 4 | 5 | Completely killed |
| | 8 | 5 | Completely killed |
| | 8 | 10 | Completely killed |
| | 8 | 20 | Completely killed |
| | 8 | 30 | Completely killed |
| | 8 | 60 | Completely killed |
| | 16 | 5 | Completely killed |
| Influenza A virus | 2 | 5 | Completely killed |
| | 4 | 5 | Completely killed |
| | 8 | 5 | Completely killed |
| | 8 | 10 | Completely killed |
| | 8 | 20 | Completely killed |
| | 8 | 30 | Completely killed |
| | 8 | 60 | Completely killed |

TABLE 8

Conductive polymer material of EX4

| Virus | Dilution factor | Incubation time (minute) | Antiviral activity |
|---|---|---|---|
| Transmissible gastroenteritis virus | 1 | 60 | Completely killed |
| | 2 | 60 | Completely killed |
| | 4 | 60 | Completely killed |
| | 8 | 60 | Completely killed |
| | 16 | 60 | Completely killed |
| Feline infectious peritonitis virus | 2 | 60 | Completely killed |
| | 4 | 60 | Completely killed |
| | 8 | 60 | Completely killed |
| | 16 | 60 | Completely killed |
| Pseudorabies virus | 2 | 0.5 | Completely killed |
| | 4 | 0.5 | Completely killed |
| | 8 | 0.5 | Completely killed |
| | 8 | 1 | Completely killed |
| | 8 | 5 | Completely killed |
| | 8 | 10 | Completely killed |
| | 8 | 20 | Completely killed |
| | 8 | 30 | Completely killed |

US 12,564,603 B2

11 12

TABLE 8-continued

| Conductive polymer material of EX4 | | | |
|---|---|---|---|
| Virus | Dilution factor | Incubation time (minute) | Antiviral activity |
| | 8 | 60 | Completely killed |
| | 16 | 0.5 | Completely killed |
| | 32 | 0.5 | Completely killed |
| | 64 | 0.5 | Completely killed |
| | 64 | 1 | Completely killed |
| | 64 | 2 | Completely killed |
| | 64 | 5 | Completely killed |
| | 64 | 10 | Completely killed |
| | 64 | 20 | Completely killed |
| | 64 | 30 | Completely killed |
| | 64 | 60 | Completely killed |

TABLE 9

| Conductive polymer material of EX5 | | | |
|---|---|---|---|
| Virus | Dilution factor | Incubation time (minute) | Antiviral activity |
| Newcastle disease virus | 2 | 30 | Completely killed |
| | 4 | 30 | Completely killed |
| | 8 | 30 | Completely killed |
| | 8 | 60 | Completely killed |
| Transmissible gastroenteritis virus | 2 | 60 | Completely killed |
| | 4 | 60 | Completely killed |
| | 8 | 60 | Completely killed |
| | 16 | 60 | Completely killed |
| | 32 | 60 | Completely killed |
| | 64 | 60 | Completely killed |
| Feline infectious peritonitis virus | 2 | 60 | Completely killed |
| | 4 | 60 | Completely killed |
| | 8 | 60 | Completely killed |
| | 16 | 60 | Completely killed |
| | 32 | 60 | Completely killed |
| | 64 | 60 | Completely killed |
| Pseudorabies virus | 2 | 5 | Completely killed |
| | 4 | 5 | Completely killed |
| | 8 | 5 | Completely killed |
| | 8 | 10 | Completely killed |

TABLE 9-continued

| Conductive polymer material of EX5 | | | |
|---|---|---|---|
| Virus | Dilution factor | Incubation time (minute) | Antiviral activity |
| | 8 | 20 | Completely killed |
| | 8 | 30 | Completely killed |
| | 8 | 60 | Completely killed |
| | 16 | 5 | Completely killed |
| | 32 | 5 | Completely killed |
| | 64 | 5 | Completely killed |
| | 64 | 10 | Completely killed |
| | 64 | 20 | Completely killed |
| | 64 | 30 | Completely killed |
| | 64 | 60 | Completely killed |
| Influenza A virus | 2 | 30 | Completely killed |
| | 4 | 30 | Completely killed |
| | 8 | 30 | Completely killed |
| | 8 | 60 | Completely killed |

Summarizing the above test results, it is clear that the conductive polymer material of the present disclosure has excellent antibacterial and antiviral activities, and hence is capable of inhibiting the growth of pathogens and inhibiting pathogenic infection.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for treating a pathogenic virus, the method comprising administering to a subject in need thereof a conductive polymer material including a conductive component,
   wherein the conductive component contains poly(3,4-ethylenedioxythiophene)-poly(styrenesulfonate), a molar ratio of poly(3,4-ethylenedioxythiophene) to poly(styrenesulfonate) in the poly(3,4-ethylenedioxythiophene)-poly(styrenesulfonate) ranging from 1:1 to 1:25, and
   wherein the pathogenic virus is selected from the group consisting of enterovirus, paramyxovirus, coronavirus, and combinations thereof.

2. The method according to claim 1, wherein the molar ratio of poly(3,4-ethylenedioxythiophene) to poly(styrenesulfonate) ranges from 1:1.5 to 1:5.

3. The method according to claim 1, wherein the conductive component further contains water.

4. The method according to claim 3, wherein the conductive polymer material further includes dimethyl sulfoxide, and a weight ratio of dimethyl sulfoxide to the conductive component is 1:33.

5. The method according to claim 1, wherein the enterovirus is enterovirus 71.

6. The method according to claim 1, wherein the paramyxovirus is newcastle disease virus.

7. The method according to claim 1, wherein the coronavirus is selected from the group consisting of feline infectious peritonitis virus (FIPV) and transmissible gastroenteritis virus (TGEV).

8. A method for reducing the growth of a pathogenic virus, the method comprising applying a conductive polymer material including a conductive component onto an object, wherein the conductive component contains poly(3,4-ethylenedioxythiophene)-poly(styrenesulfonate), a molar ratio of poly(3,4-ethylenedioxythiophene) to poly(styrenesulfonate) in the poly(3,4-ethylenedioxythiophene)-poly(styrenesulfonate) ranging from 1:1 to 1:25, and wherein the pathogenic virus is selected from the group consisting of enterovirus, paramyxovirus, coronavirus, and combinations thereof.

9. The method according to claim 8, wherein the molar ratio of poly(3,4-ethylenedioxythiophene) to poly(styrenesulfonate) ranges from 1:1.5 to 1:5.

10. The method according to claim 8, wherein the conductive component further contains water.

11. The method according to claim 10, wherein the conductive polymer material further includes dimethyl sulfoxide, and a weight ratio of dimethyl sulfoxide to the conductive component is 1:33.

12. The method according to claim 8, wherein the enterovirus is enterovirus 71.

13. The method according to claim 8, wherein the paramyxovirus is newcastle disease virus.

14. The method according to claim 8, wherein the coronavirus is selected from the group consisting of feline infectious peritonitis virus (FIPV) and transmissible gastroenteritis virus (TGEV).

\* \* \* \* \*